United States Statutory Invention Registration [19]

[11] Reg. Number: H110

Barditch et al. [45] Published: Aug. 5, 1986

[54] TRACKING OF AIR MASS MOVEMENT

[75] Inventors: Irving F. Barditch, Baltimore; Orville C. Bowersox, Frederick, both of Md.

[73] Assignee: The United States of America as represented by the Secretary of the Army, Washington, D.C.

[21] Appl. No.: 799,531

[22] Filed: Nov. 14, 1985

[51] Int. Cl.[4] ..... C12Q 1/02; C12Q 1/24; C12Q 1/04; C12Q 1/085

[52] U.S. Cl. ..... 435/29; 435/30; 435/34; 435/832

*Primary Examiner*—John F. Terapane
*Assistant Examiner*—Eric Jorgensen
*Attorney, Agent, or Firm*—Anthony T. Lane; Harold H. Card, Jr.; Edward F. Costigan

[57] ABSTRACT

The movement of an air mass is monitored by releasing a tracer entity at a given location, collecting a sample of air at a different location and analyzing the collected sample of air for the presence of the tracer entity by using *Bacillus thurengiensis* as the tracer entity and by analyzing for the presence of the bacterium by effecting a culture in a medium capable of supporting bacterial growth and preferably containing citrate as the sole source of assimilable carbon.

5 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

TRACKING OF AIR MASS MOVEMENT

BACKGROUND OF THE INVENTION

It is frequently desirable to monitor or track the movement of a mass of air. For example, air mass movement is important in weather forecasting where it is often monitored by examining changes in ambient atmospheric pressure. Studies of the phenomenon of acid rain, industrial plant emissions or of chemical or biological weapon attacks also need physical verification of the expected movement of the air masses involved in order to ascertain whether various predictions or assumptions are valid.

Theoretical discussions of air mass movement can be found in the "Air Pollution Handbook", McGill et al. (McGraw-Hill Book Co., 1956) Section 4–54 at pp. 54–59; Sutton, "Atmospheric Turbulence" (John Wiley & Sons, 1949); and Sutton, "Micrometeorology" (McGraw-Hill Book Co., 1953).

One of the present means of monitoring the movement of an air mass has been by releasing fluorescent particles of zinc cadmium sulfide or zinc sulfide into the air and sometimes by the release of a radioactive particle. A sample of the air mass is collected downwind. The presence of the fluorescent particles or radioactive particles in the collected sample is thereafter determined using suitable equipment such as, for example, a fluorometer or a radioactive counter. However, cadmium is known to be toxic and therefore its use is undesirable. It is also undesirable to release sulfides into the atmosphere or to release radioactive materials into the atmosphere. Accordingly, a need exists for a safe and reliable method of tracing air mass movement.

It is accordingly the object of this invention to provide a method for the monitoring of the movement of an air mass without the release of toxic, radioactive or other undesirable material into the atmosphere. This and other objects of the invention will become apparent to those of ordinary skill in this art from the following detailed disclosure.

SUMMARY OF THE INVENTION

This invention relates to a method of monitoring the movement of an air mass and more particularly to the monitoring of the movement of an air mass by releasing a tracer entity at a given location, collecting a sample of the air at a different location and analyzing the collected sample of air for the presence of the tracer entity in which the tracer entity is *Bacillus thurengiensis* and the analysis is effected by culturing the collected sample on a medium capable of supporting bacterium growth. Preferably, the growth medium contains citrate as the sole source of assimilable carbon.

DESCRIPTION OF THE INVENTION

In accordance with the present invention, the movement of an air mass is monitored by introducing a quantity of *Bacillus thurengiensis* into the atmosphere at one or more given locations and positioning sampling equipment one or more points of interest to collect all of the material present in the ambient air. The collection equipment is usually placed downwind of the release point, but may also be in other locations to determine if there are any unexplained or unexpected movement of the air. Frequently, a plurality of collection points forming a more or less regular grid pattern is established in order to achieve a more complete plot of the air's movement.

*Bacillus thurengiensis* is a widely used entomopathogen. It was originally isolated from natural epizootics in susceptible Lepidopteria in Japan and Germany. Various formulations of *Bacillus thurengiensis* have been commercially available for use in agriculture since the mid-1950s. A potent strain was introduced commercially in the 1970s under the trademark DIPEL. In 1977, a further strain named *Bacillus thurengiensis var israelensis* was isolated in a stagnant pool in a river bed in the Negev Desert and later designated as *Bacillus thurengiensis, Serotype H*-14. The World Health Organization has developed a standard preparation of Serotype H-14 under the designation IPS-78.

*Bacillus thurengiensis* is a spore forming, very hardy bacterium which is safe for warmblooded animals including humans. As a practical matter, the bacterium is an insecticide only for caterpillars and mosquitoes and it is not persistant in the environment. These characteristics make the *Bacillus thurengiensis* particularly useful in the present invention.

In order to trace the movement of an air mass, the bacterium is released into the atmosphere as a cloud of wet or dry particles generally, but not necessarily, in the 2–5 micron range. The bacterium can be released into the atmosphere in the same manner as it is used as a selective insecticide. For example, one can use a land-based atomizer or aerial spraying can be employed. The quantity released is not critical and theoretically a single spore is all that is necessary. More practically, a quantity of about 110–230 grams of *Bacillus thurengiensis* powder (having a potency of 1000 to 2000 Aedes Aegypti International Toxic Units) can be employed per release location but greater but lesser amounts can also be employed, if desired.

Any conventional method of collecting airborne bacteria can be employed at the collection point or points in the process of this invention. The basic methods which can be employed include impingement in liquids, impaction on solid surfaces, filtration, sedimentation, centrifugation, electrostatic precipitation and thermal precipitation. A wide variety of instruments are available for practicing these collection methods. An excellent survey of these sampling methods and the equipment employed therein can be found in "Sampling Microbiological Aerosols", Public Health Monograph No. 60, issued by the Public Health Service of the U.S. Department of Health, Education and Welfare (Public Health Service Publication No. 686).

The airborne detrius, i.e., the material found in the ambient air, various pollens, fungi, spores, soil bacteria, soil particles, soot and assorted man-made particles, in the collected sample or samples is cultured, i.e., the collected fraction of particulates in the atmosphere are combined with a suitable culture medium which can support the growth of the bacterium.

Beyond the known safety to humans, plants, domestic animals and almost all lower life forms, and the established methods of introduction into the atmosphere, the use of *Bacillus thurengiensis* is particularly advantageous for two reasons. First, the microbe grows at room temperature so that no complex equipment is needed. Second, the bacterium is unusual in that it can metabolize the citrate ion as a source of carbon while almost all other known spore forming bacteria are not so capable. Further, the inclusion of citrate in an acidic state also inhibits the growth of other microbes. These characteristics simplify the analysis procedure and provide for greater accuracy since the growth of other spore forming bacteria need not be distinguished in the medium. Accordingly, while the culture can be effected in any medium capable of supporting growth, it is preferably carried out in a medium containing citrate as the sole source of assimilable carbon. Any of the known citrate media which do not contain another assimilable carbon source can be employed.

A particular advantageous medium is the Koser Citrate Medium which in dehydrated form contains 1.5 grams of sodium ammonium phosphate, 1 gram of mono-potassium phosphate, 0.2 gram magnesium sulfate and 3 grams of sodium citrate. In this medium, the ammonium salt serves as the sole source of nitrogen and the sodium citrate as the sole source of carbon. To rehydrate this medium, 5.7 grams are dissolved in 100 ml of distilled water. Another typical citrate medium is Simmons Citrate Agar which contains 0.2 gram magnesium sulfate, 1 gram of monoammonium phosphate, 1 gram dipotassium phosphate, 2 grams sodium citrate, 5 grams sodium chloride, 15 grams agar and 0.08 gram bromthymol blue.

A typical culture medium which can be used in the present invention will contain 5.7 grams per liter Koser Citrate Medium, 10 grams per liter caseine enzymatic digest, 0.03 gram per liter $MnSO_4$, 0.02 grams per liter $FeSO_4$, 0.002 gram per liter thiamine hydrochloride and 15 grams per liter agar. Since only one *Bacillus thurengiensis* spore is needed in order to detect its presence, the test of the present invention is very sensitive. The single spore grows and replicates itself many times.

An example of one use of the present invention concerns an evaluation of the accusation that fluoride emissions from an aluminum plant was killing cattle located at a distance of about 10 miles from the production plant. A solution of *Bacillus thurengiensis* spores is sprayed into the atmosphere at the plant site under various weather conditions and collection devices are installed at the location where the cattle deaths occurred. The collected material is then cultured in the selective medium to determine the presence or absence of the bacterium. Since both the fluoride emissions and the bacterium will be carried away from the aluminum plant by the same air mass, the results of the culturing provides an indication of whether the fluoride may have traveled from the plant to the place of the cattle fatalities.

Various changes and modifications can be made in the method of this invention without departing from the spirit and scope thereof. The various embodiments which have been disclosed herein were for the purpose of further illustrating the present invention and were not intended to limit it.

What is claimed is:

1. In a method of monitoring the movement of an air mass comprising releasing a tracer entity into the atmosphere at a given location, collecting a sample of the ambient air at a different location and analyzing the sample of the collected air for the presence of the tracer entity, the improvement which comprises employing *Bacillus thurengiensis* as the tracer entity and conducting the analysis by performing a culture on the collected sample in a medium capable of supporting *Bacillus thurengiensis* growth.

2. The method of claim 1 in which samples of air are collected at a plurality of locations.

3. The method of claim 2 in which said medium contains citrate as the sole source of assimilable carbon.

4. The method of claim 3 wherein the culture medium contains Koser Citrate Medium.

5. The method of claim 1 in which said medium contains citrate as the sole source of assimilable carbon.

* * * * *